United States Patent [19]
Ikada et al.

[11] Patent Number: 5,085,632
[45] Date of Patent: Feb. 4, 1992

[54] CATHETER AND METHOD FOR THE MANUFACTURE THEREOF

[75] Inventors: Yoshito Ikada, Uji; Toshiyuki Okada, Takarazuka; Tatsuya Kawai; Michiaki Yoshimoto, both of Hiroshima, all of Japan

[73] Assignee: Japan Medical Supply Co., Ltd., Hiroshima, Japan

[21] Appl. No.: 507,376

[22] Filed: Apr. 10, 1990

[30] Foreign Application Priority Data

Aug. 10, 1989 [JP] Japan ................................ 1-207398

[51] Int. Cl.⁵ .............................................. A61M 1/00
[52] U.S. Cl. ........................................ 604/29; 604/27; 604/264; 623/12
[58] Field of Search ................. 623/1, 11, 12; 600/36; 477/2; 604/29, 27, 264, 280

[56] References Cited

U.S. PATENT DOCUMENTS

| | | | |
|---|---|---|---|
| 3,808,113 | 4/1974 | Okamura et al. | 623/1 |
| 4,167,045 | 9/1979 | Sawyer | 623/1 |
| 4,266,999 | 5/1981 | Baier | 623/11 |
| 4,373,009 | 2/1983 | Winn | 604/280 |
| 4,378,803 | 4/1983 | Takagi et al. | 604/280 |
| 4,743,258 | 5/1988 | Ikada et al. | 623/66 |
| 4,784,659 | 11/1988 | Fleckenstein et al. | 623/1 |
| 4,871,361 | 10/1989 | Kira | 623/1 |
| 4,979,959 | 12/1990 | Guire | 623/1 |

FOREIGN PATENT DOCUMENTS 119798 9/1979 Japan .

*Primary Examiner*—Randall L. Green
*Assistant Examiner*—Paul Prebilic
*Attorney, Agent, or Firm*—Kramer, Brufsky & Cifelli

[57] ABSTRACT

A catheter is provided which can be safely implanted in the living body for extended periods of time. At least that portion of the catheter which contacts the tissue comprises a cuff of porous material which is made of a vinyl alcohol polymer to which, preferably, collagen has been chemically grafted.

5 Claims, 1 Drawing Sheet

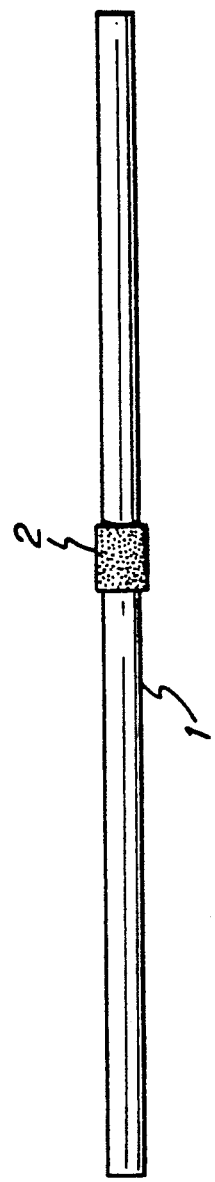

CATHETER AND METHOD FOR THE MANUFACTURE THEREOF

BACKGROUND OF THE INVENTION

1. Technical Field of the Invention

This invention relates to medical implants which can be implanted in the living body for extended periods of time and to the method for the manufacture thereof.

2. Description of the Prior Art

Whether a medical implant, such as a peritoneal catheter, can be successfully implanted in a living body for an extended period of time is highly dependant upon the manner of affixation of said device to the implanted area in the living body. For this reason, various devices are being employed to allow and accelerate the invasion of the living body tissue into the implanted area and thereupon integrate with the implanted device. The conventionally employed method is to provide the circumference of a catheter, for example, with a cuff called a "Dacron ® cuff" which consists of polyester fibers. Alternatively, catheters have been provided with cuffs made from polyurethane sponge or polyethylene sponge.

However, since polyester fibers have lesser ability to effect affixation to the living body, they tend to allow bacteria to invade into the living body, thereby often causing infection. Moreover, neither polyurethane sponge nor polyethylene sponge has provided favorable results in affixation because of their insufficient affinity to the living body. Furthermore, polyurethane sponge, when it has been implanted for a long period, has been found to deteriorate; while polyethylene sponge does not demonstrate any flexibility as a cuff.

A medical implant coated with collagen on its surface for the purpose of enhancing affinity to the living body has been disclosed in Japanese Patent Application (Laid-open) No. 119798/1979. Nevertheless, since mere coating with collagen will not assure that the collagen will become chemically combined with the substrate material, such coated material tends to peel off. To overcome such problems, it was found that the surface of the substrate could be activated by subjecting it to glow discharge or corona discharge before graft polymerizing said surface with acrylic acid so that collagen might react upon the so-modified surface and become chemically combined with the surface. The shortcoming of this method, however, is two fold; one is that it requires costly equipment and the other is uncertainty in uniformly obtaining quality products.

Accordingly, it is an object of this invention to provide medical implants which can be firmly affixed to the living body, thereby enabling the long-term implantation of such medical devices. It is another object of this invention to provide methods for the manufacture of such medical implants.

SUMMARY OF THE INVENTION

In accordance with the present invention, a medical implant is provided wherein at least that portion of the medical implant which will be in direct contact with the living body is comprised of a porous vinyl alcohol (PVA) polymer. In addition, it is considered preferable, that collagen is chemically fixed to the surface of such porous material.

Fixing collagen to the surface of said porous material can be accomplished by causing a diisocyanate compound to react upon the surface of said porous vinyl alcohol polymeric material, thereby causing the hydroxyl groups on the surface of the porous material and the diisocyanate compound to react with each other; and thereafter, allowing the grafted diisocyanate compound to react with collagen thereby chemically fixing the collagen to the porous PVA polymer.

The medical implant of the present invention maintains, when it is wetted, good flexibility and shows favorable affinity to the living body. Moreover, by fixing collagen to the surface of the porous material, living body tissue has been found to quickly invade into the pores thereof and become integrated with the living body. Accordingly, the firm affixation to the living body obtained in accordance with the present invention prevents bacteria from easily invading into the implanted area and protects said area from infection.

BRIEF DESCRIPTION OF THE DRAWINGS

The FIGURE is an illustration of a peritoneal catheter of the present invention.

DESCRIPTION OF THE PREFERRED EMBODIMENT

The present invention will be described in connection with a peritoneal catheter and vascular access port; however, it can be appreciated that these devices are simply illustrative of the medical implants which can be constructed in accordance with the present invention. The FIGURE shows a peritoneal catheter (1) with a cuff (2).

A peritoneal catheter is used as a pathway to infuse and/or drain dialysis solution to/from the abdominal cavity on peritoneal dialysis. As earlier mentioned, a cuff is provided at the implanted area around the abdominal walls. Namely, the catheter is composed of a tube, a cuff provided around the circumference of said tube and a connector which is provided at the hub of said tube. In the present invention, the cuff is composed of porous material consisting of vinyl alcohol polymer. Preferably, collagen is affixed to the surface of said porous material.

The porous material comprising vinyl alcohol polymer employed in the present invention comprises polymers wherein vinyl alcohol is the main repeating unit. Such polymers comprise not only fully saponified polyvinyl acetate but also can comprise partially saponified polyvinyl acetate and can also contain small quantities of other copolymerizable comonomers. This porous material comprising such polymers can be manufactured by the following method. The vinyl alcohol polymer can be admixed with pore-making particles to make the required material. Then, after treating the material with a suitable reagent such as formaldehyde, for cross-linking purposes, the preparation can be washed with a solvent which can dissolve and remove the pore-making particles to finally obtain the required porous material. As the pore making particles, starch is preferably used because of its safety. The resulting porous material is hard when it is dried, but it exhibits flexibility similar to that of living tissue when it is wetted.

The rate of invasion of living body tissue into the porous material varies according to the average pore size of said porous material, wherein high rates of invasion are obtained when the average pore size is between 100 and 400 μm. The highest affixation strength can be attained when the average pore size is 200 μm or less. Accordingly, porous material having an average pore size of between 100 and 200 μm is considered preferable as it has been demonstrated that the use of such porous material allows living body tissue to invade into it most quickly and become firmly affixed to said porous material.

In accordance with the present invention, the presence of hydroxyl groups on the surface of the porous material is utilized for combining collagen with the surface of said porous material. That is, vinyl alcohol polymers contain hydroxyl groups their side chain, and thus numerous hydroxyl groups exist on the surface of the porous material. These hydroxyl groups react with diisocyanate compounds such as hexamethylene diisocyanate. In the reaction, the hydroxyl groups react with an isocyanate group to form a urethane bond, thereby causing the diisocyanate compound to become grafted to the surface of the porous material. Thereafter, when causing collagen to be reacted therewith, an amino group in collagen can react with the remaining isocyanate group from the diisocyanate compound, thereby causing the collagen to indirectly combine with the porous material. The amount of collagen employed is preferably about 10 μg or more, and most preferably, about 30 μg or more per gram of said porous material.

The porous material produced in accordance with the present invention exhibits good flexibility when wetted, and thus it adapts well to the surrounding tissue.

Moreover, since the porous material to which the collagen is affixed exhibits favorable affinity, it facilitates the invasion of living body tissue into the pores and eventually results in firm affixation. Accordingly, medical implants comprised of porous PVA are suitable for long-term implantation in the living body.

This invention will be more specifically illustrated by the following examples. Unless otherwise stated, all percentages and parts are by weight.

EXAMPLE 1

Porous material consisting of polyvinyl alcohol obtained using starch as the pore-making particles and having varied average pore sizes (made by Sanwa Kako Co.) were cut into 5×5×10 mm³ test specimens. The specimens were washed with acetone and vacuum dried before being tested under the following test method. The porous materials used in this test had four different average pore sizes, i.e. 40, 150, 350 and 500 μm, respectively.

These porous materials were immersed in a solution comprising a mixture of 64 parts by volume of toluene, 16 parts by volume of hexamethylene diisocyanate and 0.02 part by volume of di-n-butyltin dilaurate at room temperature for 120 minutes, thereby causing hexamethylene diisocyanate to react upon the hydroxyl groups on the surface of these porous materials. Then, the porous materials were washed with toluene and acetone and immersed in a hydrochloric acid solution (0.001N) in which collagen (Cellmatrix Type I-P made by Nitta Gelatin K.K.) has been dissolved to prepare a solution having 0.5 mg/ml collagen concentration. Reaction was permitted to occur at 4° C. for 12 hours.

When the total combined weight of collagen affixed to the porous materials was determined by the ninhydrin method, 100–200 μg of collagen had been combined with said porous materials.

The porous materials obtained in accordance with the procedures and other porous materials to which collagen was not affixed were subcutaneously implanted in rats. Then, tissue together with the porous materials adjacent thereto were extracted from the implanted area one week later. The affixation strength between the tissue and the porous materials were measured by a tensile tester. The results are shown in Table 1.

TABLE 1

| Presence of | Average Pore Size (μm) | | | |
|---|---|---|---|---|
| Grafted Collagen | 40 | 150 | 350 | 500 |
| Yes | 475 g | 820 g | 240 g | 220 g |
| No | 380 g | 490 g | 120 g | 165 g |

It is found from the Table 1 that the porous material and the living body can be firmly affixed to each other by grafting collagen to the surface of the porous material.

EXAMPLE 2

Porous materials consisting of polyvinyl alcohol having average pore sizes of 40, 150, 350 and 500 μm, respectively, were treated in the same manner as in Example 1, and collagen was grafted to the surface of the porous materials.

The resulting porous materials were subcutaneously implanted in rats, and after the lapse of the prescribed period of time, the extent of invasion of living body tissue into the porous materials was observed through a microscope. The results thereof are shown in Table 2.

TABLE 2

| Implanted | Average Pore Size (μm) | | | |
|---|---|---|---|---|
| Period | 40 | 150 | 350 | 500 |
| 1 Week | X | Δ | Δ | X |
| 3 Weeks | Δ | ◯ | Δ | Δ |
| 6 Weeks | Δ | ◯ | ◯ | ◯ |
| 9 Weeks | ◯ | ◯ | ◯ | ◯ |

Degree of invasion of tissue into the porous material:
X: Very scarcely invaded
Δ: Considerably invaded
◯: Completely invaded The results set forth in Table 2 clearly show that invasion of tissue was observed during the first week of implantation in the porous materials having average pore sizes of 150 μm or 350 μm, while no invasion of tissue was observed during the first week of implantation for any other average pore size. It can be seen that average pore sizes ranging from 100–400 μm are suitable to allow living body tissue to invade into the porous material.

For comparison purposes, implantation tests were conducted with porous material having an average pore size of 40 μm and to which collagen had not been grafted.

After three weeks, observation showed that tissue invasion into the porous material was scarce. This test result indicates that the porous materials to which collagen has been grafted permit rapid invasion of living body tissue into the pores thereof.

COMPARATIVE EXAMPLE 1

Porous material consisting of polyethylene was treated with corona discharge, then acrylic acid was graft copolymerized with said material and thereafter collagen was caused to react with it to affix collagen to the surface of said porous material. The porous material prepared in the above manner and other non-treated porous polyethylene material were subcutaneously implanted in rats in the same manner as in Example 2, then the extent of invasion of tissue into the porous materials was observed through a microscope. The results indicated that no invasion of tissue into the non-treated porous material was observed even after nine weeks, and only about half of the collagen-fixed porous material was invaded by tissue after nine weeks.

EXAMPLE 3

Three different types of vascular access ports were prepared: (1) porous material consisting of polyvinyl alcohol to which collagen had been grafted in the same manner as in Example 1; (2) porous material consisting of polyethylene to which collagen had been grafted in the same manner as in Comparative Example 1; and (3) porous material consisting of polyethylene to which collagen had not been grafted were respectively used at the implanted areas. Each of these porous materials were percutaneously implanted in the back of seven rabbits each, then the occurrence of infection in each of them was macroscopically observed once a week. The results of above tests indicated no single case of infection recognized in any of the test rabbits which had been implanted with the porous materials consisting of polyvinyl alcohol to which collagen had been grafted by the end of the 30th week; one case of infection was recognized in one rabbit which had been implanted with porous material consisting of polyethylene to which collagen has been grafted, by the end of the 5th week. In addition, with porous material consisting of polyethylene to which collagen was not grafted, infected cases occurred in one rabbit by the end of the 2nd week, in three rabbits by the end of the 3rd week, in one rabbit by the end of the 7th week, in one rabbit by the end of the 10th week and, by the end of the 30th week, there was only one rabbit left which had not become infected.

It is seen from the above results that the medical implants of the present invention are essentially free from bacterially-induced infection.

Since the medical implants of the present invention are flexible in the living body, patients hardly feel the presence of any foreign body within their body. Furthermore, such flexibility essentially precludes damage to living body tissue. Still further, the porous material combined with collagen grafted to its surface exhibits higher affinity to tissue, and thus facilitates invasion by living body tissue into the porous material as well as firm affixation thereto.

Accordingly, by applying this invention to a cuff for a peritoneal catheter, a vascular access port or another medical implant, the occurrence of microbial infection within the implanted area can be reduced to a minimum.

Moreover, since the medical implants of the present invention do not require any highly sophisticated surface treatment such as glow discharge or corona discharge, manufacture of such implants can be readily accomplished while assuring constant and stable quality.

What is claimed is:

1. A catheter comprising a tube and a cuff provided around the circumference of said tube, wherein the cuff comprises a porous material consisting essentially of a vinyl alcohol polymer having collagen chemically grafted to the surface of the porous material.

2. A catheter as defined in claim 1, wherein the average pore size of said porous material ranges from about 100 to about 400 $\mu$m.

3. A catheter as defined in claim 2, wherein the average pore size of said porous material ranges from about 100 to about 200 $\mu$m.

4. A catheter as defined in claim 1, wherein the collagen is present in an amount of at least about 10 $\mu$g/gm of porous material.

5. A catheter as defined in claim 1, wherein the average pore size of the porous material ranges from about 100 to about 400 $\mu$m.

* * * * *